United States Patent
Yu et al.

(10) Patent No.: US 8,733,149 B2
(45) Date of Patent: May 27, 2014

(54) FILM BULK ACOUSTIC WAVE RESONATOR-BASED ETHANOL AND ACETONE SENSORS AND METHODS USING THE SAME

(75) Inventors: Hongyu Yu, Tempe, AZ (US); Xiaotun Qiu, Tempe, AZ (US)

(73) Assignee: Arizona Board of Regents, a body corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/513,283

(22) PCT Filed: Jan. 20, 2011

(86) PCT No.: PCT/US2011/021809
§ 371 (c)(1),
(2), (4) Date: Jun. 1, 2012

(87) PCT Pub. No.: WO2011/091107
PCT Pub. Date: Jul. 28, 2011

(65) Prior Publication Data
US 2012/0297859 A1    Nov. 29, 2012

Related U.S. Application Data

(60) Provisional application No. 61/296,696, filed on Jan. 20, 2010.

(51) Int. Cl.
*G01N 33/497* (2006.01)
*G01N 29/036* (2006.01)

(52) U.S. Cl.
USPC ............................ 73/23.3; 73/24.01

(58) Field of Classification Search
USPC ................................. 73/23.3, 24.01
See application file for complete search history.

(56) References Cited

U.S. PATENT DOCUMENTS

| | | | |
|---|---|---|---|
| 6,839,946 B2 | 1/2005 | Ylilammi et al. | |
| 7,364,551 B2 | 4/2008 | Allen et al. | |
| 2004/0107765 A1 | 6/2004 | Lee et al. | |
| 2006/0032312 A1 | 2/2006 | Auner et al. | |
| 2008/0004542 A1* | 1/2008 | Allen et al. | 600/532 |
| 2008/0163694 A1 | 7/2008 | Haskell et al. | |
| 2009/0112115 A1* | 4/2009 | Huang et al. | 600/532 |

OTHER PUBLICATIONS

Rosenbaum, Joel F. Bulk Acoustic Wave Theory and Devices. 1988. Artech House.*

(Continued)

*Primary Examiner* — Irving A Campbell
(74) *Attorney, Agent, or Firm* — McDonnell Boehnen Hulbert & Berghoff LLP

(57) ABSTRACT

The present invention relates generally to the detection of alcohol. The present invention relates more particularly to the film bulk acoustic wave resonator-based devices, and their use in the sensing of ethanol and/or acetone. One aspect of the invention is a method for detecting ethanol, acetone or both in a gaseous sample including: providing a film bulk acoustic wave resonator having a zinc oxide piezoelectric layer; exposing the film bulk acoustic wave resonator to the gaseous sample; determining the resonant frequency of the film bulk acoustic wave resonator; and determining the concentration of ethanol, the concentration of acetone, or both in the gaseous sample using the resonant frequency of the film bulk acoustic wave resonator.

19 Claims, 8 Drawing Sheets

(56) References Cited

OTHER PUBLICATIONS

Aronava M et al. (2003). "Combinatorial libraries of semiconductor gas sensors as inorganic electronic noses," Appl. Phys. Lett. 83: 1255-1257.
Baik N et al. (2000). "Hydrothermally treated sol solution of tin oxide for thin film gas sensor," Sens. Actuators B 63: 74-79.
Cao W et al. (2007). "Current Status of Methods and Techniques for Breath Analysis," Crit. Rev. Anal. Chem. 37: 3-13.
Chakraborty S et al. (2006). "Selective detection of methane and butane by temperature modulation in iron doped tin oxide sensors," Sens. Actuators B. 115: 610-613.
Chen Y et al. (2006). "Linear ethanol sensing of $SnO_2$ nanorods with extremely high sensitivity," Appl. Phys. Lett. 88: 083105.
Cheng W et al. (1999). "Technology development in breath microanalysis for clinical diagnosis," J. Lab. Clin. Med. 133: 218-228.
Chiorino A et al. (1999). "Preparation and characterization of $SnO_2$ and $MoO_x$—$SnO_2$ nanosized powders for thick film gas sensors," Sens. Actuators B 58: 338-349.
Choi U.-S. et al. (2005). "Sensing properties of Au-loaded $SnO_2$—$Co_3O_4$ composites to CO and $H_2$," Sens. Actuators B 107: 397-401.
De Lacy Costello B et al. (2002). "Highly sensitive mixed oxide sensors for detection of ethanol," Sens. Actuators B 87: 207-210.
De Lacy Costello B et al. (2003). "Thick film organic vapour sensors based on binary mixtures," Sens. Actuators B 92: 159-166.
Engstrom J et al. (2000). "Combinatorial materials science: paradigm shift in materials discovery and optimization," AIChE J. 46: 2-5.
Eranna G et al. (2004). "Oxide Materials for Development of Integrated Gas Sensors—A Comprehensive Review," Crit. Rev. Solid State Mat. Sci. 29: 111-188.
Fleischer M et al. (2002). "Detection of volatile compounds correlated to human diseases through breath analysis with chemical sensors," Sens. Actuators B 83: 245-249.
Gong H et al. (1999). "Interaction between thin-film tin oxide gas sensor and five organic vapors," Sens. Actuators B 54: 232-235.
Ho J.-J. et al. (1998). "High sensitivity and ethanol gas sensor integrated with a solid-state heater and thermal isolation improvement structure of legal drink-drive limit detecting," Sens. Actuators B 50: 227-233.
Huang J et al. (2006). "Temperature modulation and artificial neural network evaluation for improving the CO selectivity of $SnO_2$ gas sensor," Sens. Actuators B 114: 1059-1063.
Huo L et al. (2005). "Sol-gel route to pseudocubic shaped $Fe_2O_3$ alcohol sensor: preparation and characterization," Sens. Actuators B 107: 915-920.
Hyodo T et al. (2003). "Gas-sensing properties of ordered mesoporous $SnO_2$ and effect of coatings thereof," Sens. Actuators B 93: 590-600.
Ivanovskaya M et al. (2003). "Gas-sensitive properties of thin film heterojunction structures based on $Fe_2O_3$—$In_2O_3$ nanocomposites," Sens. Actuators B 93: 422-430.
Ivanovskaya M et al. (2003). "Influence of chemical composition and structural factors of $Fe_2O_3/In_2O_3$ sensors on their selectivity and sensitivity to ethanol," Sens. Actuators B 96: 498-503.
Jiang Y et al. (2006). "Electrical conductivity and gas sensitivity to VOCs of V-doped $ZnFe_2O_4$ nanoparticles," Mater. Lett. 60: 1374-1378.
Jing Z et al. (2006). "Preparation and gas sensing properties of pure and doped $Fe_2O_3$ by an anhydrous solvent method," Sens. Actuators B 113: 177-181.
Jing Z et al. (2006). "Synthesis, characterization and gas sensing properties of undoped and Co-doped $Fe_2O_3$-based gas sensors," Mater. Lett. 60: 952-956.
Jinkawa T et al. (2000). "Relationship between ethanol gas sensitivity and surface catalytic property of tin oxide sensors modified with acidic or basic oxides," J. Mol. Catal. A Chem. 155: 193-200.
Kim K et al. (2007). "The selective detection of $C_2H_5OH$ using $SnO_2$—ZnO thin film gas sensors prepared by combinatorial solution deposition," Sens. Actuators. B. 123: 318-324.

Li H et al. (2005). "Zinc oxide films prepared by sol-gel method," J. Cryst. Growth 275: e943-e946.
Li X et al. (2006). "Synthesis, characterization, and gas-sensor application of $WO_3$ nanocuboids," J. Electrochem. Soc. 153:H133-H137.
Liu Y et al. (2005). "A highly sensitive and fast-responding $SnO_2$ sensor fabricated by combustion chemical vapor deposition," Chem. Mater. 17: 3997-4000.
Lord H et al. (2002). "Breath Analysis and Monitoring by Membrane Extraction with Sorbent Interface," Anal. Chem. 74: 5650-5657.
Mukhopadhyay R (2004). "Don't waste your breath," Anal. Chem. 76: 273A-276A.
Nakagawa H et al. (2000). "An automated car ventilation system," Sens. Actuators B 65: 133-137.
Neri G et al. (2005). "A study of the catalytic activity and sensitivity to different alcohols of $CeO_2$-$Fe_2O_3$ thin films," Sens. Actuators B 111-112: 78-83.
Peng L et al. (2008). "Light induced enhancing gas sensitivity of copper-doped zinc oxide at room temperature." Sens. Actuators B. 131: 660-664.
Qiu X et al. (2009). "Film bulk acoustic-wave resonator based ultraviolet sensor," Appl. Phys. Lett. 94: 151917.
Qiu X et al. (2010). "Film bulk acoustic-wave resonator based relative humidity sensor using ZnO films," Electrochemical and Solid-State Letters 13: J65-J67.
Qiu X et al. (2010). "Acetone sensor based on Film Bulk Acoustic Resonator." 2010 IEEE Sensors, 1546-1549.
Reddy C et al. (2002). "Preparation of $Fe_2O_3(0.9)$-$SnO_2(0.1)$ by hydrazine method: application as an alcohol sensor," Sens. Actuators B 81: 170-175.
Reddy C et al. (2003). "Selective detection ethanol vapor using $xTiO_2$-$(1-x)WO_3$ based sensor," Sens. Actuators B 94: 99-102.
Righettoni M et al. (2010). "Si: $WO_3$ Sensors for Highly Selective Detection of Acetone for Easy Diagnosis of Diabetes by Breath Analysis," Anal. Chem. 82: 3581-3587.
Ryabsev S et al. (1999). "Application of semiconductor gas sensors for medical diagnostics," Sens. Actuators B 59: 26-29.
Sahay P (2005). "Zinc oxide thin film gas sensor for detection of acetone," J. Mater. Sci. 40: 4383-4385.
Sahay P et al. (2005). "Sprayed ZnO thin films for ethanol sensors," J. Mater. Sci. 40: 4791-4793.
Sanchez J et al. (2003). "GC Analysis of Human Breath with a Series-Coupled Column Ensemble and a Multibed Sorption Trap," Anal. Chem. 75: 2231-2236.
Shimizu Y et al. (1999). "Effect of surface modification on $NO_2$ sensing properties of $SnO_2$ varistor-type sensors," Sens. Actuators B 60: 118-124.
Smith D et al. (2005). "Selected ion flow tube mass spectrometry (SIFT-MS) for on-line trace gas analysis," Mass Spectrom. Rev. 24: 661-700.
Takata M et al. (1976). "Dependence of electrical conductivity of ZnO on degree of sintering," J. Am. Ceram. Soc. 59: 4-8.
Tamaki J et al. (1998). "Dilute hydrogen sulfide sensing properties of CuO—$SnO_2$ thin film prepared by low-pressure evaporation method," Sens. Actuators B 49: 121-125.
Toda K et al. (2006). "Measurement of ammonia in human breath with a liquid-film conductivity sensor," Anal. Chem. 78: 7284-7291.
Tsuboi T et al. (1999). "Thermal oxidation of acetone behind reflected shock wave," in: Proceedings of the 17th International Colloquium on the Dynamics of Explosions and Reactive Systems, Heidelberg, Germany, Jul. 25-30, 1999.
Ueda M et al. (2008). "Development of an X-Band Filter Using Air-Gap-Type Film Bulk Acoustic Resonators," Jpn. J. Appl. Phys. 47: 4007-4010.
Wan Q et al. (2004). "Fabrication and ethanol sensing characteristics of ZnO nanowire gas sensors," Appl. Phys. Lett. 84: 3654-3656.
Wessler B et al. (2004). "Combinatorial synthesis of thin film libraries for microwave dielectrics," Appl. Surf. Sci. 223: 30-34.
Xie H et al. (2006). "Gas sensor arrays based on polymer carbon black to detect organic vapors at low concentration," Sens. Actuators B 113: 887-891.
Xue X et al. (2005). "Synthesis and ethanol sensing properties of $ZnSnO_3$ nanowires," Appl. Phys. Lett. 86: 233101-233103.

(56) References Cited

OTHER PUBLICATIONS

Yamazoe N et al. (2008). "Theory of power laws for semiconductor gas sensors," Sens. Actuators. B. 128: 566-573.

Yamazoe N (2005). "Toward innovations of gas sensor technology," Sens. Actuators B. 108: 2-14.

Yu J.-B. et al. (2005). "Analysis of diabetic patient's breath with conducting polymer sensor array," Sens. Actuators B 108: 305-308.

Zhang G.-Y. et al. (2006). "$MCo_2O_4$ (M=Ni, Cu, Zn) nanotubes: template synthesis and application in gas sensors," Sens. Actuators B 114: 402-409.

Zhang H et al. (2005). "Micromachined Acoustic Resonant Mass Sensor," J. Microelectromech. Syst. 14: 699-706.

Zhao J et al. (2006). "Alcohols and acetone sensing properties of $SnO_2$ thin films deposited by dip-coating," Sens. Actuators B 115: 460-464.

Zhu B et al. (2004). "Improvement in gas sensitivity of ZnO thick film to volatile organic compounds (VOCs) by adding $TiO_2$," Mater. Lett. 58: 624-629.

Zvyagin A et al. (2010). "Determination of Acetone and Ethanol Vapors Using Semiconductor Sensors." J. Anal. Chem. 65: 94-98.

International Search Report of International Patent Application No. PCT/US2011/021809, filed Jan. 20, 2011, mailed Sep. 16, 2011.

Written Opinion of International Patent Application No. PCT/US2011/021809, filed Jan. 20, 2011, mailed Sep. 16, 2011.

\* cited by examiner

FILM BULK ACOUSTIC WAVE RESONATOR-BASED ETHANOL AND ACETONE SENSORS AND METHODS USING THE SAME

CROSS-REFERENCE TO RELATED APPLICATIONS

This application claims the priority of U.S. Provisional Patent Application Ser. No. 61/296,696, filed Jan. 20, 2010, which is hereby incorporated herein by reference in its entirety.

BACKGROUND OF THE INVENTION

1. Field of the Invention

The present invention relates generally to the detection of ethanol and/or acetone. The present invention relates more particularly to the film bulk acoustic wave resonator-based devices, and their use in the sensing of ethanol and/or acetone.

2. Technical Background

Driving under the influence of alcohol is a serious traffic violation; such behavior causes many accidents and deaths on the road. Electrochemical breath alcohol analyzers are generally used as a quick and reliable screening device at sobriety checkpoints and after motorists are pulled over on suspicion of DUI. However, acetone can strongly interfere with electrochemical detection. Acetone is generally considered to be the only endogenous volatile organic compound that is a potentially interfering substance in breath alcohol analysis. It is present in the breath of a normal person, and in increased concentrations as the result of prolonged fasting, use of ketogenic diets, or diabetes. Moreover, breath acetone itself can be an analyte of interest for medical diagnostic purposes. The analysis of exhaled breath for acetone can help to provide an express non-invasive diagnosis of ketosis.

In conventional sensors, ethanol and acetone can interfere with one another. Accordingly, drunkenness can wrongly be interpreted as ketosis, and vice versa. Ethanol and acetone can be distinguished using electrochemical or infrared instruments in commercial breath alcohol analyzers. However, they are complex and expensive, and specific training is required in order to become a proficient user. Resistivity-based metal oxide sensors have been developed, which can have relatively simple structures and can be cost effective and easy to use. Their main drawback is that they can not effectively distinguish ethanol and acetone. Because they use the change in resistivity as the gas detecting signal, both ethanol and acetone will share a similar response: a decrease in resistivity. Resistivity-based ethanol sensors based on zinc oxide thin films have been extensively investigated. Special attention is given to discriminating between ethanol and acetone due to their similar chemical nature. However, as both gases can reduce the resistivity of the sensor, the selectivity was not as high as desirable. Selected ion flow tube mass spectrometry has shown great potential in real-time concentration monitoring of acetone and ethanol in human breath. While it is highly selective and sensitive, its high cost and limited portability hinder its usefulness as a standard diagnostic tool.

SUMMARY OF THE INVENTION

In certain aspects, the present invention relates to ethanol and/or acetone sensing using a zinc oxide-based film bulk acoustic-wave resonator. Film bulk acoustic-wave resonators more generally have been drawing considerable attention both as filters and as high sensitivity mass sensors in recent years. In certain aspects of this invention, film bulk acoustic-wave resonator is used to measure ethanol concentration in the environment. This method can address one of the most challenging problems in ethanol and/or acetone sensing: the discrimination between ethanol and acetone. In certain aspects of the invention as described herein, the resonant frequency of a zinc oxide-based film bulk acoustic-wave resonator device increases with increasing acetone concentration, but decreases with increasing ethanol concentration. This opposite responsivity can allow ethanol and acetone to be distinguished from one another.

According to one aspect of the invention, a method for detecting ethanol and/or acetone in a gaseous sample includes:
  providing a film bulk acoustic wave resonator having a zinc oxide piezoelectric layer;
  exposing the film bulk acoustic wave resonator to the gaseous sample;
  determining the resonant frequency of the film bulk acoustic wave resonator; and
  determining the concentration of ethanol, acetone or both in the gaseous sample using the resonant frequency of the film bulk acoustic wave resonator.

According to another aspect of the invention, a breath alcohol and/or acetone analyzer comprises a film bulk acoustic wave resonator having a zinc oxide piezoelectric layer; and a circuit adapted to determine an ethanol concentration, an acetone concentration, or both of a gaseous sample using a resonant frequency measured by the resonant frequency measuring circuit.

BRIEF DESCRIPTION OF THE DRAWINGS

The accompanying drawings are not necessarily to scale, and sizes of various elements can be distorted for clarity.

DETAILED DESCRIPTION OF THE INVENTION

Zinc oxide is a promising material for ethanol sensing applications. Ethanol sensors based on zinc oxide thin films have been extensively investigated. See, e.g., P. P. Sahay et al., *J. Mater. Sci.*, 40 (2005), pp. 4791-4793, which is hereby incorporated herein by reference in its entirety. Special attention has been paid to discrimination between acetone and ethanol due to their similar chemical nature and presence in the breath of subjects of breath alcohol tests. For example, Kim and his coworkers used combinational solution deposition to prepare various $SnO_2$—ZnO thin film sensors, which exhibited different sensitivities for acetone and ethanol. *Sens. Actuators. B.*, 123 (2007), pp. 318-324, which is hereby incorporated herein by reference in its entirety. However, as both gases reduced the resistivity of the sensor, the selectivity was not as high as desirable. In this disclosure, a zinc oxide-based film bulk acoustic wave resonator device is provided which has opposing responses to acetone and ethanol. Such opposite responses can advantageously provide for relatively higher sensitivity and discrimination between acetone and ethanol.

Figure 1:
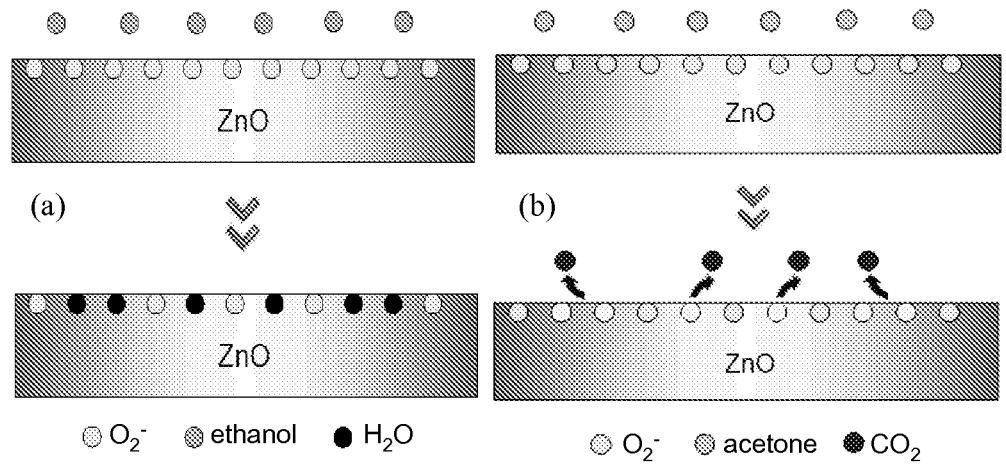
FIG. 1 is a pair of schematic diagrams illustrating a proposed sensing mechanism for (a) ethanol and (b) acetone.

Without intending to be bound by theory, the inventors propose the following mechanism for the opposite response to ethanol and acetone. Ethanol reacts with adsorbed oxygen ions on the ZnO surface and generates water which is adsorbed by the ZnO, as shown in FIG. 1(a). Accordingly, the density of the film increases, resulting in a frequency decrease. See X. Qiu et al., *Appl. Phys. Lett.*, 94 (2009), 151917, which is hereby incorporated herein by reference in its entirety. Acetone, on the other hand, reacts with the surface adsorbed oxygen ions on the zinc oxide film and releases $CO_2$ as a reaction product, as shown in FIG. 1(b). P. P. Sahay, *J. Mater. Sci.*, 40 (2005), pp. 4383-4385, which is hereby incorporated herein by reference in its entirety. Accordingly, the density of the film decreases, resulting in a frequency increase.

One aspect of the invention is a method for detecting ethanol and/or acetone in a gaseous sample. The detection can be, for example, a simple yes-no detection of a threshold level of ethanol, acetone or both, or alternatively a determination of a concentration of ethanol, acetone, or both. The concentrations of ethanol, acetone or both can themselves be reported, or alternatively one or both of the concentrations can be related to some other desired quantity (e.g., a blood alcohol level of a subject, or ketosis level of a subject).

According to this aspect of the invention, one step in a method for detecting ethanol, acetone, or both in a gaseous sample is the provision of a film bulk acoustic-wave resonator having a zinc oxide piezoelectric layer. Particular embodiments of such film bulk acoustic-wave resonators are described in more detail below. The film bulk acoustic wave resonator is exposed to the gaseous sample. The resonant frequency of the film bulk acoustic wave sensor is determined. For example, in certain embodiments, the resonant frequency of the film bulk acoustic wave sensor is determined both before and after exposure to the gaseous sample, so that the difference in resonant frequency upon exposure can be measured. In other embodiments, the resonant frequency is determined only after exposure to the gaseous sample; in such embodiments, a known value of the initial resonant frequency can be used. In certain embodiments, the resonant frequency is measured as a function of time, for example so that the time scale of absorption/desorption of acetone and/or ethanol is known.

Finally, the concentrations of ethanol, acetone, or both in the gaseous sample are determined using the determined resonant frequency (or frequencies) of the film bulk acoustic wave sensor. As described in more detail below, and demonstrated by the examples herein, as a result of the zinc oxide material used in the piezoelectric layer, the resonant frequency of the film bulk acoustic-wave resonator increases with exposure to acetone vapor, and decreases with exposure to ethanol vapor. The person of skill in the art can use a calibration curve, for example, to correlate the determined resonant frequency (or frequencies) with the concentration of ethanol, the concentration or ethanol, or both. The concentrations of ethanol, acetone, or both in the gaseous sample can be determined as an actual concentration (e.g., in ppm). Alternatively, the concentrations of ethanol, acetone, or both can be reported as to whether they meet some threshold level (e.g., a level of ethanol that would constitute driving while impaired). The concentration of ethanol can alternatively or also be determined as some other value correlated with the concentrations of ethanol, acetone, or both in the gaseous sample. For example, a blood alcohol level can be determined from the concentration of ethanol in the gaseous sample, or directly determined from the determined resonant frequency (or frequencies). Similarly, a concentration of acetone in a bodily fluid (e.g., in blood, or an equivalent concentration to urine) can be determined from the concentration of acetone in the gaseous sample, or directly determined from the determined resonant frequency (or frequencies). As used herein, the term "determining the concentration of ethanol in the gaseous sample" includes the determination of any value or property correlated with ethanol concentration in the gaseous sample, regardless of whether a numerical value of ethanol concentration in the gaseous sample is actually determined. Similarly, as used herein, the term "determining the concentration of acetone in the gaseous sample" includes the determination of any value or property correlated with acetone concentration in the gaseous sample, regardless of whether a numerical value of acetone concentration in the gaseous sample is actually determined.

Figure 2:
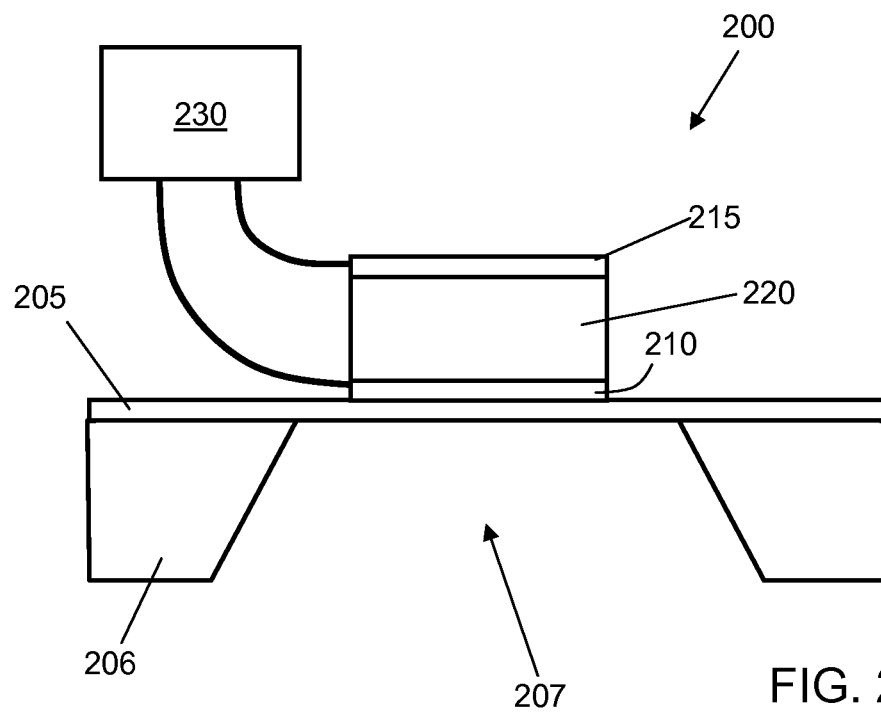
FIG. 2 is a schematic cross-sectional view of a film bulk acoustic wave resonator suitable for use according to certain embodiments of the invention.

One embodiment of a film bulk acoustic wave resonator suitable for use in the methods described herein is shown in schematic cross-sectional view in FIG. 2. Film bulk acoustic wave resonator 200 includes a diaphragm layer 205, suspended above a void space 207. The diaphragm layer can, for example, be suspended by a substrate 206, as shown in the embodiment of FIG. 2. A first electrode layer 210 is disposed on the diaphragm layer 205, and a zinc oxide piezoelectric layer 220 is disposed on the first electrode 210. A second electrode layer 215 is disposed on the zinc oxide piezoelectric layer 220. A resonant frequency measuring circuit 230 is operatively coupled to the first electrode 210 and the second electrode 215. While in the embodiment of FIG. 2, the zinc oxide piezoelectric layer is shown as being in contact with the electrodes, the person of skill in the art will recognize that other layers (e.g., dielectric layers) can be disposed between the electrodes, between the first electrode and the diaphragm layer, and/or on the second electrode.

Examples of thicknesses for the various layers in this embodiment include:
  diaphragm layer: up to 2.0 µm thick (e.g., in the range of 0.1 µm to 2.0 µm);
  first electrode layer: 0.1-1.0 µnm thick;
  zinc oxide piezoelectric layer: 0.2-5.0 µm thick; and/or
  second electrode layer: 0.1-1.0 µm thick.

Figure 3:
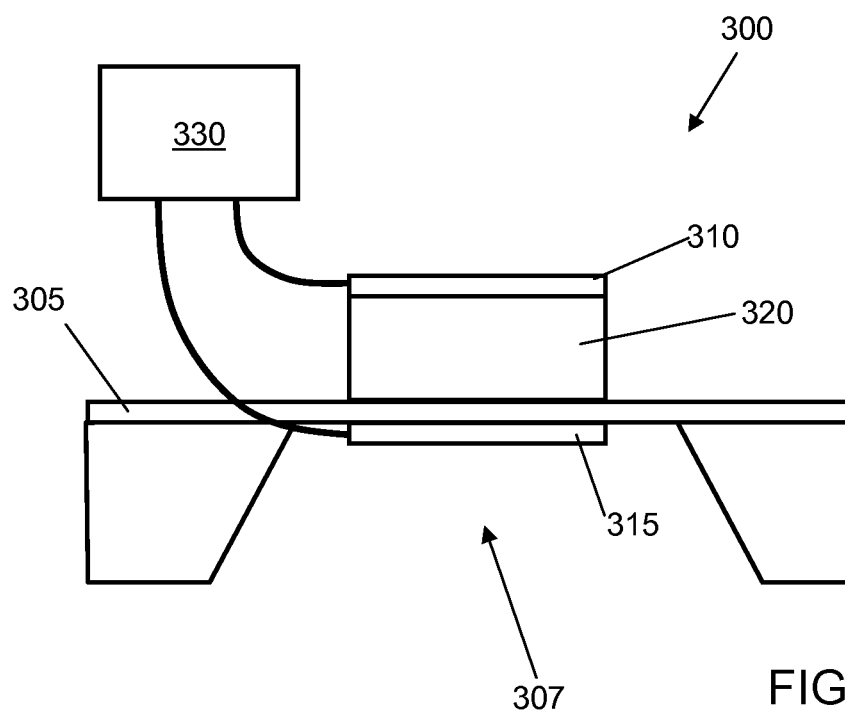
FIG. 3 is a schematic cross-sectional view of a film bulk acoustic wave resonator suitable for use according to other embodiments of the invention.

Another embodiment of a film bulk acoustic wave resonator suitable for use in the methods described herein is shown in schematic cross-sectional view in FIG. 3. Film acoustic wave resonator 300 includes a diaphragm layer 305, suspended above a void space 307, and having a first side and a second side. A zinc oxide piezoelectric layer 320 is disposed on the first side of the diaphragm layer, and a first electrode layer 310 is disposed on the zinc oxide piezoelectric layer 320. A second electrode layer 315 is disposed on the second side of the diaphragm layer, such that the diaphragm layer and the zinc oxide piezoelectric layer are both disposed between the first and second electrodes. A resonant frequency measuring circuit 330 is operatively coupled to the first electrode layer and the second electrode layer.

Examples of thicknesses for the various layers in this embodiment include:

diaphragm layer: 0.1-2.0 μm thick;
zinc oxide piezoelectric layer: 0.2-5.0 μm thick;
first electrode layer: 0.1-1.0 μm thick; and
second electrode layer: 0.1-1.0 μm thick.

The diaphragm layer can be made of a variety of substances. For example, in one embodiment, the diaphragm layer is made from silicon nitride. In other embodiments, the diaphragm layer can be made from silicon dioxide. The person of skill in the art can select other substances for use in the diaphragm layer.

The devices described above with reference to FIGS. 2 and 3 include a diaphragm layer. Similar devices can be made without a diaphragm layer. In such embodiments, one or more of the other layers of the device can extend to the substrate, thereby supporting the resonator structure. A diaphragm layer can be used in the fabrication process to support device layers as they are grown, then removed to provide a diaphragm-free device.

The electrode layers can be made of a variety of substances. For example, in certain embodiments, the second electrode layer is made from gold (optionally deposited on a thin layer of chromium to enhance adhesion). In certain embodiments, the first electrode layer is made from aluminum. Of course, other materials can be used for the electrodes, such as molybdenum, platinum, aluminum or gold/chromium.

The various elements can be formed in a variety of shapes and sizes. As the person of skill in the art will recognize, the sensitivity and resonant frequency of the device can depend on the shapes, thicknesses and sizes of the various elements. For example, in one embodiment, the zinc oxide piezoelectric layer can have a surface area in the range of 0.0025 $mm^2$ to 0.2 $mm^2$. In certain embodiments, the shapes, thicknesses and sizes of the various elements are selected to yield a resonant frequency in the range of 0.2 GHz to 10 GHz.

The zinc oxide layer can be, for example, substantially crystalline. In one embodiment, the zinc oxide layer is substantially crystalline with its wurzite C axis substantially perpendicular to its opposed surfaces.

The measurement can be performed at a wide variety of temperatures. It may be desirable to include a temperature sensor (e.g., a thermistor) near the film bulk acoustic wave resonator, in order to allow temperature calibration. Accordingly, in certain embodiments, the determination of the concentration of ethanol, the concentration of acetone, or both in the gaseous sample takes into account the temperature of the measurement.

As described in more detail below, the zinc oxide-based film bulk acoustic wave resonator sensor can discriminate acetone from ethanol. Accordingly, in certain embodiments of the invention, the gaseous sample contains both acetone and ethanol.

As described in more detail below, the zinc oxide-based film bulk acoustic wave resonator sensor will exhibit opposite frequency shifts for ethanol and acetone. As mentioned above, resistivity-based alcohol sensors (such as resistive zinc oxide alcohol sensors) will provide changes in resistance in the same direction with ethanol and acetone. One example of a resistivity-based metal oxide sensor is described in Kim, K., et al., Sens. Actuators. B., vol. 123, p. 318 (2007), which is hereby incorporated herein by reference in its entirety. Similarly, Righettoni and his coworkers developed a Si-doped $WO_3$ nanoparticle film-based acetone sensor with minimal response to ethanol. Anal. Chem., vol. 82, pp. 3581-3587 (2010), which is hereby incorporated herein by reference in its entirety. Exposing a gaseous sample to both a zinc-oxide based film bulk acoustic wave resonator sensor and a resistivity-based sensor and comparing the results will allow the person of skill in the art to cancel out the effect of acetone on the measurement of ethanol and provide a more accurate ethanol measurement; and can allow the person of skill in the art to cancel out the effect of ethanol on the measurement of acetone and provide a more accurate acetone measurement. Accordingly, in one embodiment of the methods described herein, a method further includes: providing a resistivity-based ethanol and/or acetone sensor; exposing the resistivity-based sensor to the gaseous sample at substantially the same time as the film bulk acoustic wave resonator is exposed to the gaseous sample; determining the resistivity of the resistivity-based sensor; and using the resistivity of the resistivity-based sensor along with the resonant frequency of the film bulk acoustic wave sensor in determining the concentration of ethanol, the concentration of acetone, or both. The use of both the resistivity of the resistivity-based sensor and the resonant frequency of the film bulk acoustic wave sensor in determining the concentration of ethanol in certain embodiments can be used to substantially cancel out any effect of acetone on the determination of the concentration of ethanol. Similarly, the use of both the resistivity of the resistivity-based sensor and the resonant frequency of the film bulk acoustic wave sensor in determining the concentration of acetone in certain embodiments can be used to substantially cancel out any effect of ethanol on the determination of the concentration of acetone.

In another embodiment, ultraviolet light can be used to alter the sensing performance of the film bulk acoustic wave resonator. Ultraviolet (UV) light can degrade the response to ethanol, but enhance the response to acetone. Accordingly, by determining resonant frequency both with and without UV radiation, the person of skill in the art can substantially cancel out the effect of acetone on the measurement of ethanol, and/or substantially cancel out the effect of ethanol on the measurement of acetone. The determination with and without UV radiation can be performed sequentially using a single film bulk acoustic wave resonator, or using two different, closely spaced film bulk acoustic wave resonators, one with a UV source configured to illuminate it. See L. Peng, T. Xie, M. Yang, P. Wang, D. Xu, S. Pang, and D. Wang, Sens. Actuators. B., 131 (2008), pp. 660-664, which is hereby incorporated herein by reference in its entirety.

In certain embodiments, the film acoustic wave sensor is configured to change its resonant frequency substantially linearly with ethanol concentration throughout the range of about 100 ppm to about 250 ppm. This range is especially relevant to detecting the breath alcohol content of a person at 0.08 grams of alcohol/210 liters breath (which corresponds to about 186 ppm ethanol). Accordingly, in certain embodiments, the gaseous sample is the breath of a human subject.

The person of skill in the art can use standard calibration techniques to determine the concentration of ethanol. A computer or microprocessor can, for example, be used to convert the determined resonant frequency or frequencies into an ethanol concentration (e.g., a blood alcohol content), an acetone concentration (e.g., a blood acetone concentration) or both. As the person of skill in the art, one or more calibration curves can be used in performing the calculations.

In another aspect of the invention, a breath alcohol analyzer comprises a film bulk acoustic wave resonator having a zinc oxide piezoelectric layer; and a circuit adapted to determine an alcohol concentration of a gaseous sample using a resonant frequency measured by the resonant frequency measuring circuit. The film bulk acoustic wave resonator can, for example, be as described herein. The resonant frequency measuring circuit can be coupled to a system for determining a concentration of ethanol in a gaseous sample (e.g., a blood alcohol content), as described above.

In another aspect of the invention, a breath acetone analyzer comprises a film bulk acoustic wave resonator having a zinc oxide piezoelectric layer; and a circuit adapted to determine an acetone concentration of a gaseous sample using a resonant frequency measured by the resonant frequency measuring circuit. The film bulk acoustic wave resonator can, for example, be as described herein. The resonant frequency measuring circuit can be coupled to a system for determining a concentration of acetone in a gaseous sample (e.g., a blood acetone content), as described above.

EXAMPLES

Certain aspects of the invention are described in more detail in the following Examples. The Examples demonstrate ethanol and acetone sensing using a zinc oxide based film bulk acoustic wave resonator. The resonant frequency of the film bulk acoustic wave resonator decreases as the concentration of ethanol increased with a detection limit around 1 ppm. The resonant frequency of the film bulk acoustic wave resonator increases as the concentration of acetone increased with a detection limit around 4 ppm. Accordingly, these two gases can be distinguished due to their opposite response. Furthermore, the fact that the sensor can detect the presence of ethanol in the mixture of acetone and ethanol validates its selectivity. Ultraviolet (UV) light was applied to monitor its effects on the gas sensing performance of the film bulk acoustic wave resonator. It degraded the response to ethanol, while enhanced the response to acetone.

Figure 4:
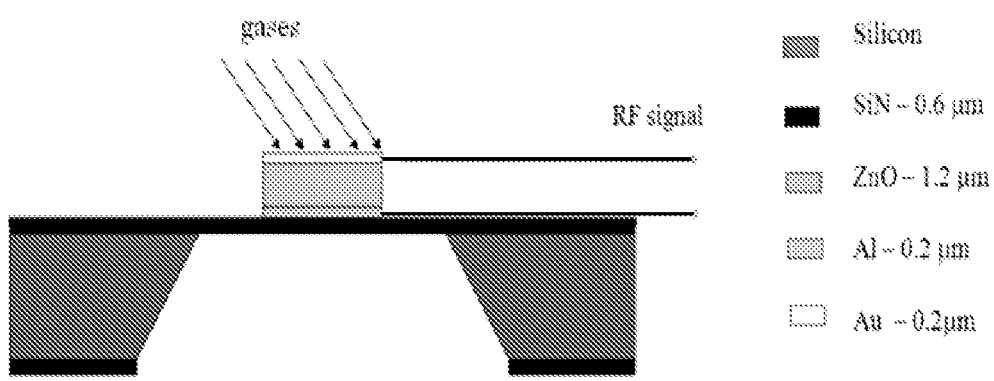
FIG. 4 is a schematic cross-sectional view of a film bulk acoustic wave resonator used in the experiments described in the Examples.

The schematic structure of the film bulk acoustic wave resonator used in the first set of experiments described herein is shown in FIG. 4. A sputtered ZnO film acts both as the ethanol sensitive layer and the piezoelectric actuation layer for the film bulk acoustic wave resonator sensor. The resonant frequency of the film bulk acoustic wave resonator was around 1.4 GHz. The quality factor (Q) of the film bulk acoustic wave resonator was about 550. Top and bottom schematic perspective views of the film bulk acoustic wave resonator are provided in FIG. 5, and a photomicrograph is shown in FIG. 6. The shape of the resonator is roughly pentagonal with each side measuring about 75 µm. The sensing area was about 0.026 mm$^2$.

Figure 5:
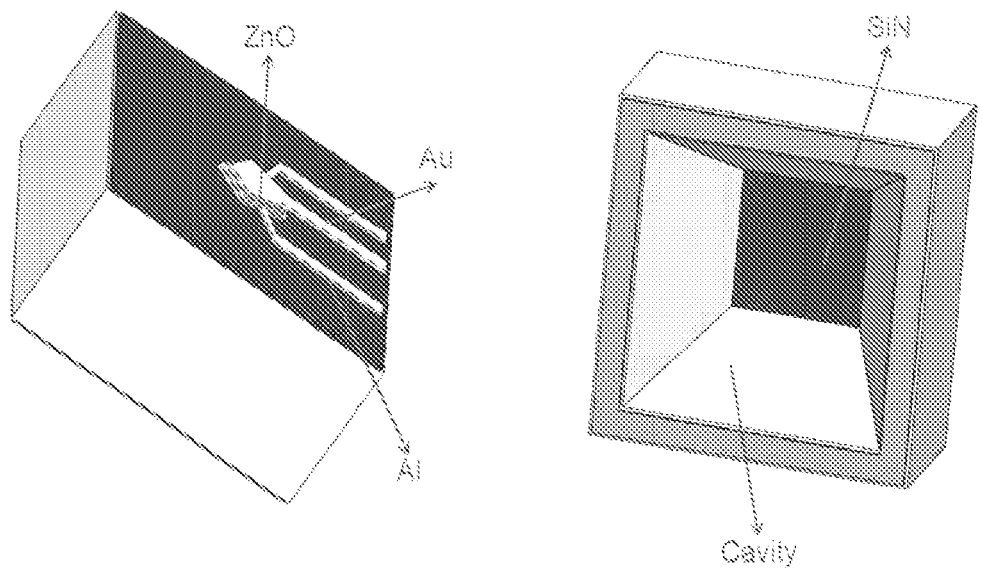
FIG. 5 provides top and bottom schematic perspective views of the film bulk acoustic wave resonator used in the experiments described in the Examples.
Figure 6:
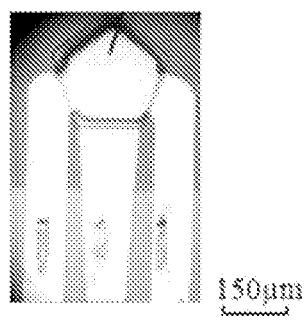
FIG. 6 is a photomicrograph of the film bulk acoustic wave resonator used in the experiments described in the Examples.
Figure 7:
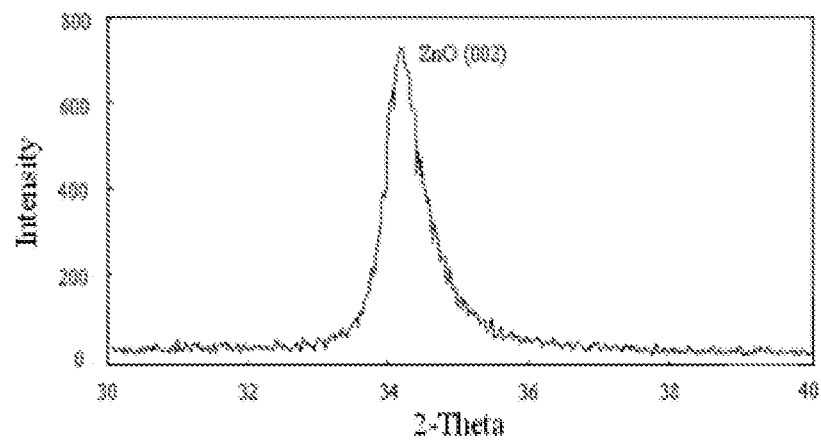
FIG. 7 is an x-ray diffraction pattern of the zinc oxide layer of the device of FIGS. 4-6.

The film bulk acoustic wave resonator of FIGS. 4-6 is built on a silicon nitride diaphragm (0.6 µm thick). A radio-frequency sputtered zinc oxide (ZnO) film (1.2 µm thick) acted both as the gas sensitive layer and the piezoelectric actuation layer for the film bulk acoustic wave resonator. The zinc oxide film was formed as wurzite, with its C axis alignment perpendicular to the plane of the zinc oxide layer, as evidenced by the x-ray diffraction pattern of FIG. 7.

The top and bottom electrodes were formed from Au (0.2 µm thick) and Al (0.2 µm thick), respectively.

The fabrication process of the film bulk acoustic wave resonator sensor was as follows. In the first step, a silicon nitride layer was deposited on a silicon wafer (100) with low-pressure chemical vapor deposition (LPCVD). The silicon nitride film was patterned by reactive ion etching (RIE). Then the Si wafer was etched from the backside anisotropically in potassium hydroxide (KOH) to form a cavity, extending substantially to the silicon nitride film, thereby suspending it over the cavity. Next, the bottom Al electrode was deposited by electron-beam evaporation and patterned on top of the silicon nitride film by wet chemical etching. Zinc oxide was RF sputtered and etched to form the desired pattern. The last step was the electron-beam deposition and patterning of the top Au electrode by lift-off. Notably, the top electrode did not form a completely conformal coating on the zinc oxide as a result of the surface roughness of the film. Accordingly, there are discontinuities in the top electrode that can allow gases to reach the zinc oxide.

The device was encapsulated in a chamber to control the gas concentration. The device was tested on a probe station with Ground-Signal-Ground 150 micron pitch probes from Cascade Microtech Inc. The calibration was carried out with an impedance standard substrate using a short-open-load (SOL) method. The resonant frequency was monitored with an Agilent E5071C network analyzer and recorded using a LabVIEW program. The concentration of the ethanol and acetone was calculated from the volume of the vapor and that of the chamber. We also did calibration using Draeger gas detection pumps and tubes as reference.

Figure 8:
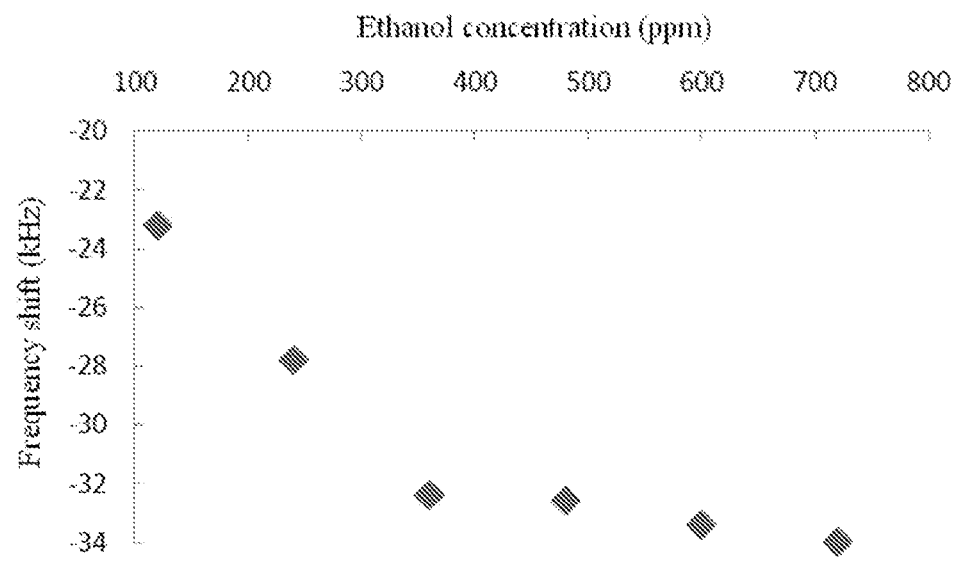
FIG. 8 is a graph showing the response of a film bulk acoustic wave resonator to ethanol.

The response of the film bulk acoustic wave resonator to ethanol is shown in FIG. 8. The resonant frequency decreased as the concentration of ethanol increased. With 120 ppm ethanol, the frequency shift was −23.2 kHz. As the concentration increased to 720 ppm, the frequency shift was −34 kHz, reaching saturation.

Figure 9:
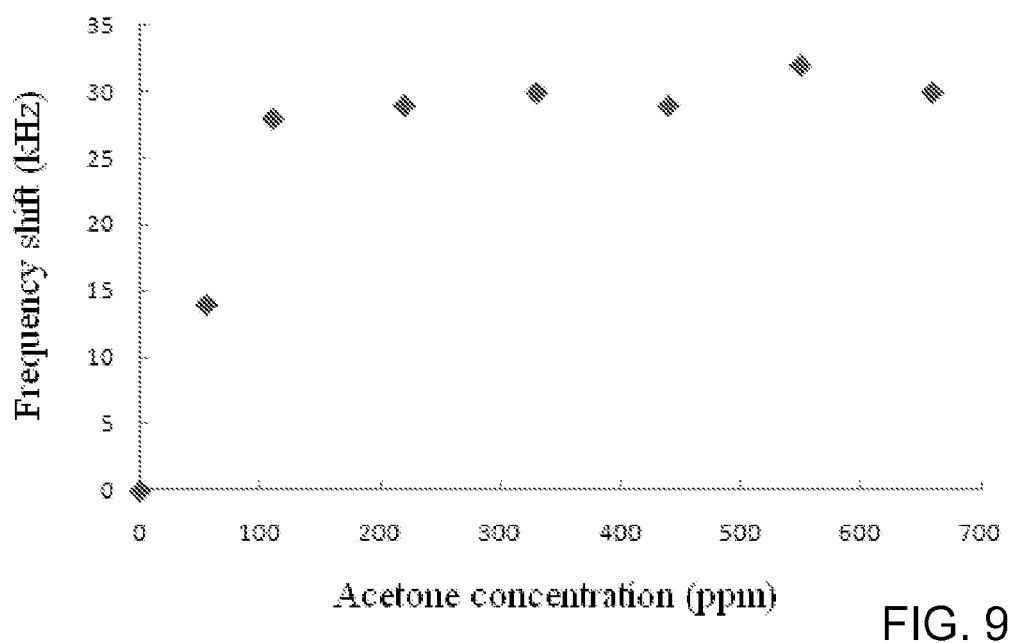
FIG. 9 is a graph showing the response of a film bulk acoustic wave resonator to acetone.

The response of the film bulk acoustic wave resonator to acetone is shown in FIG. 9. For 55 ppm acetone, the frequency upshift was 14 kHz. As the concentration increased to 220 ppm, the frequency upshift rose to 30 kHz, reaching saturation.

Figure 10:
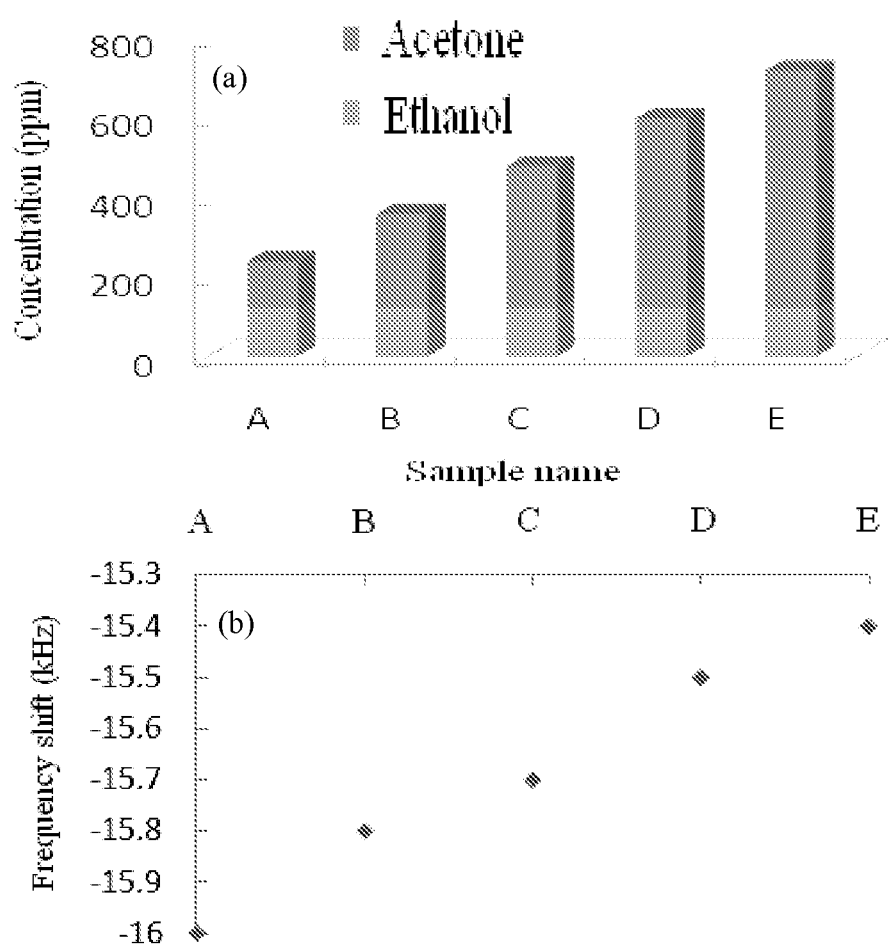
FIG. 10 are graphs showing (a) concentrations of ethanol/acetone mixtures; and (b) response to mixtures of ethanol and acetone.

In another experiment, ethanol was mixed with different amounts of acetone to test the selectivity of the sensor. FIG. 10(a) provides the total concentrations of acetone and ethanol; the volume ratio between ethanol and acetone changed from 1:1 to 1:5. FIG. 10(b) provides frequency shift data for the concentrations of FIG. 10(a). Notably the film bulk acoustic wave resonator was able to detect the presence of ethanol with a frequency drop for all the samples. Moreover, although the acetone concentration increased by fivefold across the experimental data, the frequency shift only increased by less than 1 kHz. Accordingly, the zinc oxide based system has high selectivity for ethanol.

Figure 11:
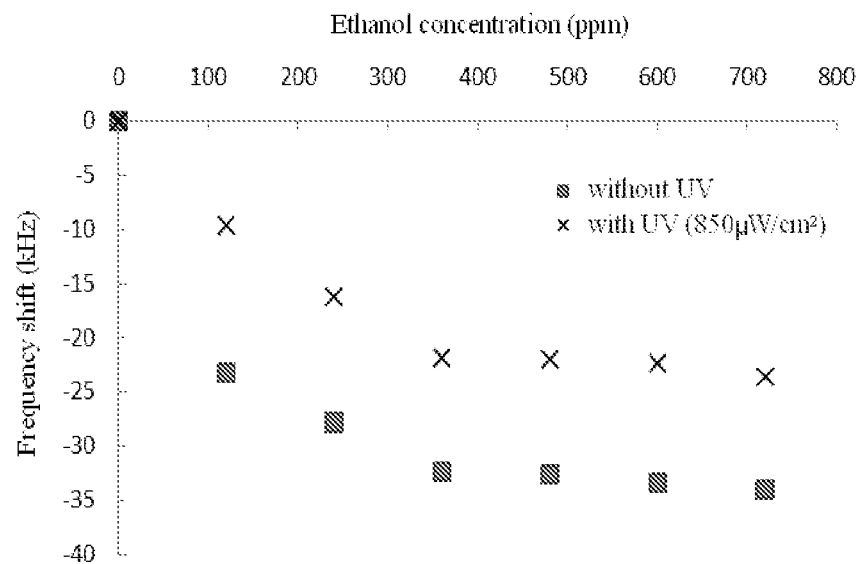
FIG. 11 is a graph showing response to ethanol with and without ultraviolet radiation.
Figure 12:
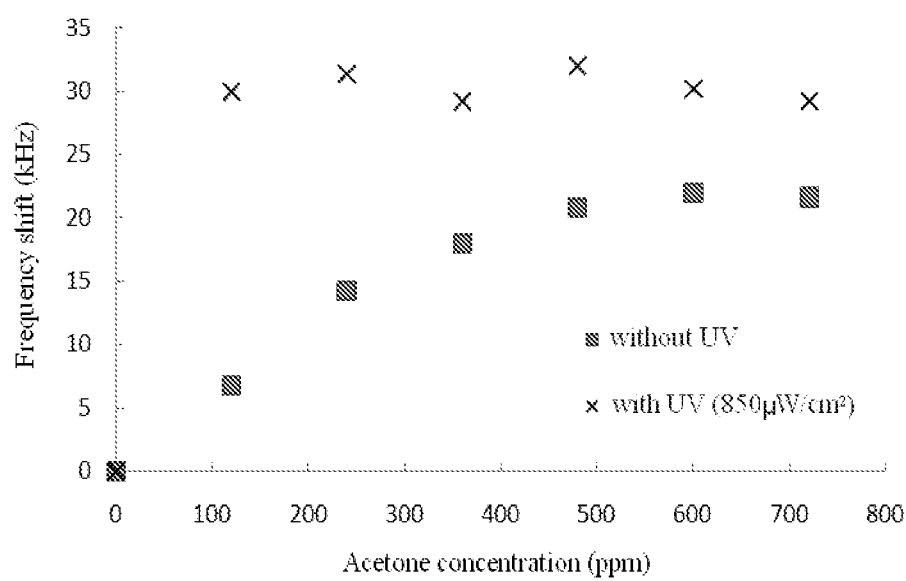
FIG. 12 is a graph showing response to acetone with and without ultraviolet radiation.

The effects of UV irradiation on the gas sensing performance of the film bulk acoustic wave resonator was monitored. UV radiation degraded the response to ethanol, as shown in FIG. 11. Without UV radiation, 120 ppm ethanol vapor caused a frequency shift of −23.2 kHz; with UV radiation (wavelength 365 nm, 850 µW/cm$^2$), the response was −9.6 kHz. In contrast, UV radiation enhanced the response to acetone, as shown in FIG. 12. Without UV radiation, 120 ppm acetone vapor the frequency shift was +6.8 kHz; with UV radiation (wavelength 365 nm, 850 µW/cm$^2$), the response increased to +30 kHz. Moreover, the response saturated even at 120 ppm. Without intending to be bound by theory, the inventors propose the following mechanism for the effect of UV radiation on the response to ethanol and acetone. UV has a photocatalytic effect on the interaction between both acetone and ethanol with the surface adsorbed oxygen ions to enhance the reaction. Therefore, for acetone, the frequency upshift increased, and saturated even with a concentration as low as 120 ppm. For ethanol, however, as the reaction between ethanol and oxygen ions was enhanced, more water was generated and adsorbed on the film surface. The water prevented ethanol from diffusing into the zinc oxide film for further reaction, resulting in a smaller response.

Figure 13:
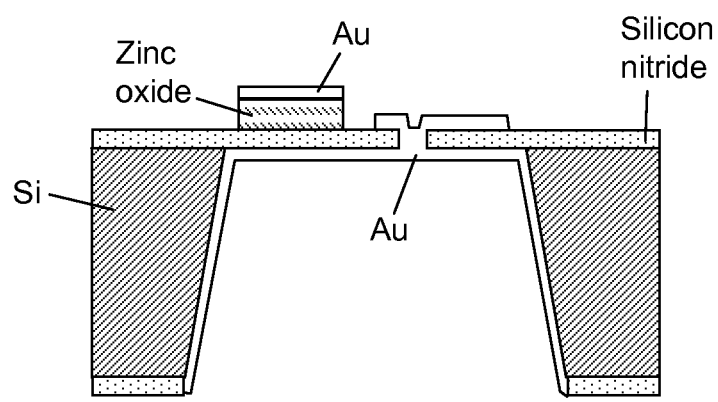
FIG. 13 is a schematic cross-sectional view of a film bulk acoustic wave resonator suitable for use according to certain embodiments of the invention.
Figure 14:
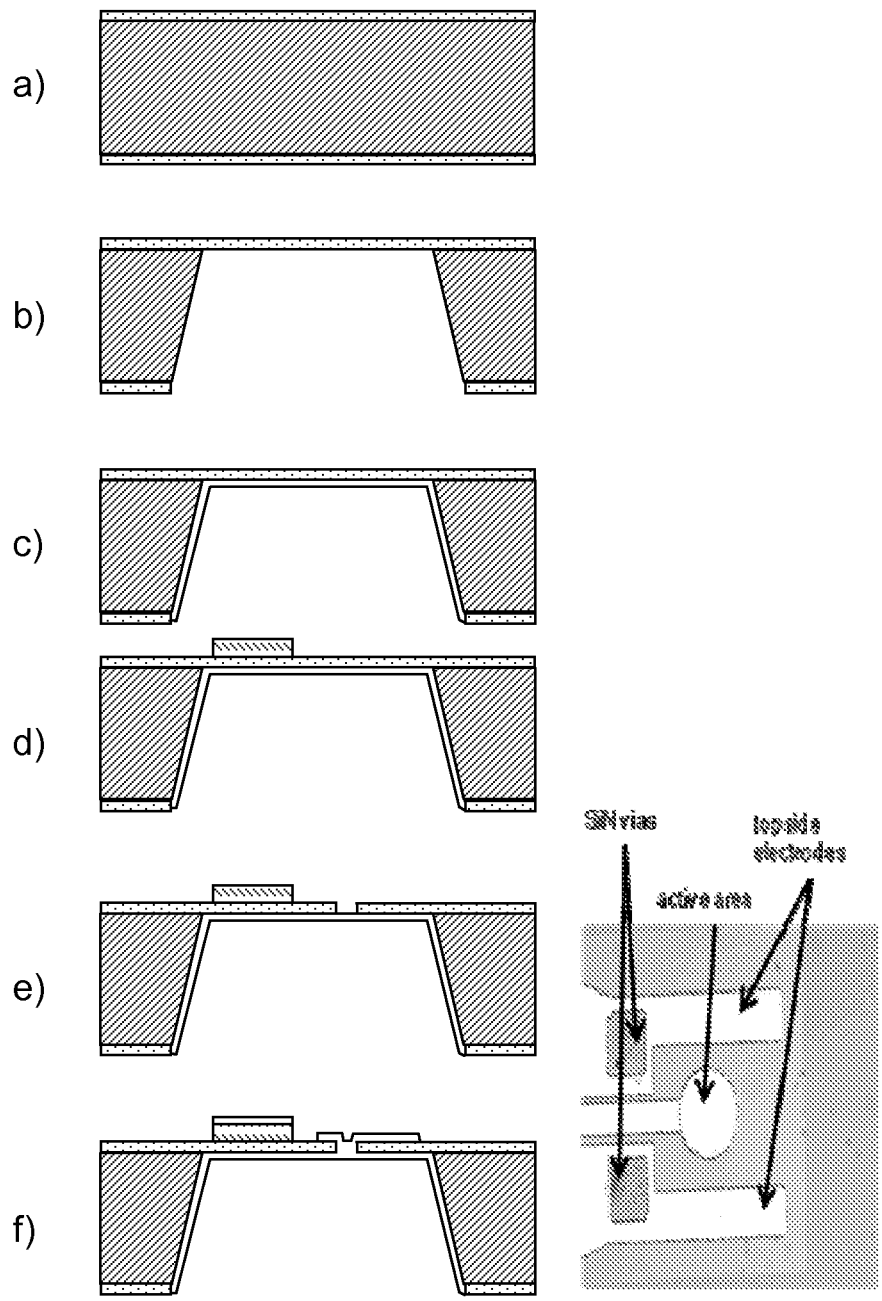
FIG. 14 is a schematic depiction of a process for making the film bulk acoustic wave resonator of FIG. 13, and a photomicrograph of the resonator so made.

The schematic structure of an alternate film bulk acoustic wave resonator for use in the present invention is shown in schematic cross-sectional view in FIG. 13. A fabrication process flow is shown in schematic view in FIG. 14. First, (a) low-stress silicon-rich silicon nitride is deposited (0.3 µm) on the silicon wafer. Then, (b) the backside silicon nitride is patterned with reactive ion etching (RIE) and the silicon is anisotropically etched through with potassium hydroxide to form the silicon nitride diaphragm. Next, (c) layers of chromium and gold are deposited (0.01 µm/0.1 µm) onto the backside. On the top side (d) the piezoelectric semiconductor material, zinc oxide (ZnO), is sputter-deposited (0.62 µm) and patterned on the silicon nitride diaphragm. This step is followed by (e) RIE etching of vias through the silicon nitride, exposing the backside metal. Finally, (f) chromium and gold are deposited (0.01 µm/0.1 µm) and patterned on the topside, providing a topside connection to the backside metal.

Unless clearly excluded by the context, all embodiments disclosed for one aspect of the invention can be combined with embodiments disclosed for other aspects of the invention, in any suitable combination.

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A method for detecting ethanol and acetone in a gaseous sample, the method comprising
providing a film bulk acoustic wave resonator having a zinc oxide piezoelectric layer;
exposing the film bulk acoustic wave resonator to the gaseous sample;
determining the resonant frequency of the film bulk acoustic wave resonator; and
determining the concentration of ethanol and acetone in the gaseous sample using the resonant frequency of the film bulk acoustic wave resonator, wherein the resonant frequency of the film bulk acoustic-wave resonator increases with exposure to acetone vapor and decreases with exposure to ethanol vapor.

2. The method according to claim 1, wherein the film bulk acoustic wave resonator comprises:
a first electrode layer;
the zinc oxide piezoelectric layer disposed on the first electrode;
a second electrode layer disposed on the zinc oxide piezoelectric layer; and
a resonant frequency measuring circuit operatively coupled to the first electrode and the second electrode.

3. The method according to claim 2, wherein
the zinc oxide piezoelectric layer has a thickness in the range of 0.2 µm to 5.0 µm;
the first electrode layer has a thickness in the range of 0.1 µm to 1.0 µm; and
the second electrode layer has a thickness in the range of 0.1 µm to 1.0 µm.

4. The method according to claim 2, further comprising a diaphragm layer having a thickness in the range of 0.1 µm to 2 µm, upon which the first electrode layer is disposed.

5. The method according to claim 4, wherein
the diaphragm layer has a thickness up to 2.0 µm;
the zinc oxide piezoelectric layer has a thickness in the range of 0.2 µm to 5.0 µm;
the first electrode layer has a thickness in the range of 0.1 µm to 1.0 µm; and
the second electrode layer has a thickness in the range of 0.1 µm to 1.0 µm.

6. The method according to claim 2, wherein the zinc oxide piezoelectric layer has a surface area in the range of 0.0025 $mm^2$ to 0.2 $mm^2$.

7. The method according to claim 1, wherein the film bulk acoustic wave resonator comprises:
a diaphragm layer suspended above a void space, the diaphragm layer having a first side and a second side;
a zinc oxide piezoelectric layer disposed on the first side of the diaphragm layer;
a first electrode layer disposed on the zinc oxide piezoelectric layer;
a second electrode layer disposed on the second side of the diaphragm layer; and
a resonant frequency measuring circuit operatively coupled to the first electrode layer and the second electrode layer.

8. The method according to claim 1, wherein the zinc oxide layer is substantially crystalline, with its wurtzite C axis is substantially perpendicular to its opposed surfaces.

9. The method according to claim 1, wherein the film bulk acoustic wave resonator has a resonant frequency in the range of 0.2 GHz to 10 GHz.

10. The method according to claim 1, wherein the film bulk acoustic wave resonator is configured to change its resonant frequency substantially linearly with ethanol concentration throughout the range of about 100 ppm to about 250 ppm.

11. The method according to claim 1, wherein the gaseous sample is the breath of a human subject.

12. The method of claim 1, wherein the resonant frequency of the film bulk acoustic wave resonator is determined both with and without ultraviolet irradiation.

13. A breath alcohol analyzer comprising a film bulk acoustic wave resonator having a zinc oxide piezoelectric layer; and a resonant frequency measuring circuit adapted to determine an ethanol concentration and an acetone concentration of a gaseous sample using a resonant frequency measured by the resonant frequency measuring circuit, wherein the resonant frequency of the film bulk acoustic-wave resonator increases with exposure to acetone vapor and decreases with exposure to ethanol vapor.

14. The analyzer according to claim 13, wherein the film bulk acoustic wave resonator comprises:
a first electrode layer;
the zinc oxide piezoelectric layer disposed on the first electrode;
a second electrode layer disposed on the zinc oxide piezoelectric layer; and
the resonant frequency measuring circuit operatively coupled to the first electrode layer and the second electrode layer.

15. The analyzer according to claim 14, wherein
the zinc oxide piezoelectric layer has a thickness in the range of 0.2 μm to 5.0 μm;
the first electrode layer has a thickness in the range of 0.1 μm to 1.0 μm; and
the second electrode layer has a thickness in the range of 0.1 μm to 1.0 μm.

16. The analyzer according to claim 14, further comprising a diaphragm layer having a thickness up to 2 μm, upon which the first electrode layer is disposed.

17. The analyzer according to claim 14, wherein the zinc oxide piezoelectric layer has a surface area in the range of 0.0025 mm$^2$ to 0.2 mm$^2$.

18. The analyzer according to claim 13, wherein the zinc oxide layer is substantially crystalline, with its wurtzite C axis is substantially perpendicular to its opposed surfaces.

19. The analyzer according to claims 13, wherein the resonant frequency measuring circuit is operatively coupled to a system for determining a concentration of ethanol and acetone in a gaseous sample.

* * * * *